(12) United States Patent
Kocaturk et al.

(10) Patent No.: US 10,695,540 B2
(45) Date of Patent: Jun. 30, 2020

(54) SEGMENTED METALLIC GUIDEWIRES

(71) Applicant: The United States of America, as represented by the Secretary, Department of Health and Human Services, Bethesda, MD (US)

(72) Inventors: Ozgur Kocaturk, Rockville, MD (US); Burcu Basar, Washington, DC (US); Robert J. Lederman, Chevy Chase, MD (US)

(73) Assignee: The United States of America, as Represented by the Secretary, Department of Health and Human Services, Bethesda, MD (US)

(*) Notice: Subject to any disclaimer, the term of this patent is extended or adjusted under 35 U.S.C. 154(b) by 527 days.

(21) Appl. No.: 15/514,744

(22) PCT Filed: Oct. 19, 2015

(86) PCT No.: PCT/US2015/056266
§ 371 (c)(1),
(2) Date: Mar. 27, 2017

(87) PCT Pub. No.: WO2016/064753
PCT Pub. Date: Apr. 28, 2016

(65) Prior Publication Data
US 2017/0239450 A1 Aug. 24, 2017

Related U.S. Application Data

(60) Provisional application No. 62/066,167, filed on Oct. 20, 2014.

(51) Int. Cl.
*A61M 25/09* (2006.01)
*A61B 5/055* (2006.01)
(Continued)

(52) U.S. Cl.
CPC .......... *A61M 25/09* (2013.01); *A61B 5/055* (2013.01); *A61M 2025/09075* (2013.01);
(Continued)

(58) Field of Classification Search
CPC ........ A61B 5/055; A61M 2025/09075; A61M 2025/09108; A61M 2025/09133;
(Continued)

(56) References Cited

U.S. PATENT DOCUMENTS

2003/0069520 A1 4/2003 Skujins et al.
2003/0120148 A1 6/2003 Pacetti
(Continued)

FOREIGN PATENT DOCUMENTS

DE 10 2007 016674 10/2008
WO WO 02/084316 10/2002
(Continued)

OTHER PUBLICATIONS

International Search Report and Written Opinion for related International Application No. PCT/US2015/056266, dated Apr. 14, 2016.

*Primary Examiner* — Michael T Rozanski
(74) *Attorney, Agent, or Firm* — Klarquist Sparkman, LLP (57) ABSTRACT

Disclosed herein are embodiments of segmented metallic guidewires that are suitable for MRI catheterization. Disclosed guidewires comprise a plurality of short conductive metallic segments that individually are short enough such that they do not resonate during MRI. The conductive segments are electrically insulated from each other and mechanically coupled together end-to-end via connectors, such as stiffness matched connectors, to provide a sufficiently long, strong, and flexible guidewire for catheterization that is non-resonant during MRI.

30 Claims, 6 Drawing Sheets

(51) Int. Cl.
*G01R 33/36* (2006.01)
*G01R 33/28* (2006.01)

(52) U.S. Cl.
CPC ............. *A61M 2025/09108* (2013.01); *A61M 2025/09133* (2013.01); *G01R 33/286* (2013.01); *G01R 33/288* (2013.01); *G01R 33/3685* (2013.01)

(58) Field of Classification Search
CPC ... A61M 25/09; G01R 33/286; G01R 33/288; G01R 33/3685
See application file for complete search history.

(56) References Cited

U.S. PATENT DOCUMENTS

| | | |
|---|---|---|
| 2004/0254450 A1 | 12/2004 | Griffin et al. |
| 2010/0063383 A1 | 3/2010 | Anderson et al. |

FOREIGN PATENT DOCUMENTS

| | | |
|---|---|---|
| WO | WO 2008/034010 | 3/2008 |
| WO | WO 2009/146339 | 12/2009 |

SEGMENTED METALLIC GUIDEWIRES

CROSS-REFERENCE TO RELATED APPLICATIONS

This is the U.S. National Stage of International Application No. PCT/US2015/056266, filed Oct. 19, 2015, which was published in English under PCT Article 21(2), and which claims the benefit of U.S. Provisional Patent Application No. 62/066,167 filed Oct. 20, 2014. The provisional application is incorporated by reference herein in its entirety.

FIELD

This application is related to guidewires, such as for catheter-based medical procedures, and particularly to guidewires for use during magnetic resonance imaging (MRI).

BACKGROUND

Catheter-based intravascular procedures typically require an initial insertion of a guidewire followed by other instrumentation. Conventional guidewires are made of a long, metal wire in order to provide sufficient mechanical strength and flexibility to enable catheter procedures. However, such guidewires cannot be safely used during MRI procedures because the guidewire is electrically conductive and resonates in response to the electromagnetic field applied during the MRI procedure, which can result in excess heating, vibration, and/or other problems. Non-metallic guidewires can lack sufficient torquability and column strength and are therefore insufficiently safe for many procedures. Hybrid designs can be prone to mechanical failure at the junctures between the components.

SUMMARY

Disclosed herein are embodiments of segmented metallic guidewires that can flex and torque like non-segmented guidewires and that are suitable for MRI catheterization. Disclosed guidewires comprise a plurality of short conductive segments that individually are electrically short enough such that the segments do not resonate during MRI, such as when using a 1.5T MRI scanner. The conductive segments are electrically insulated from each other and mechanically coupled together end-to-end via connectors, such as stiffness matched connectors, to provide a sufficiently long, strong, and flexible guidewire for catheterization that is non-resonant (e.g., prevents standing wave formation) during MRI. The stiffness matched rods and connectors can provide more even bending over the length of the transitions between the metallic rods (e.g., instead of increased bending at the joints between the metallic rods), which can result in enhanced column strength of the guidewire.

Disclosed embodiments comprise a plurality of metallic rods positioned in axial alignment along a longitudinal axis of the guidewire, wherein the metallic rods are electrically insulated from each other, and a plurality of connectors, with each connector positioned at a joint between two of the insulated metallic rods such that each connector secures two of the metallic rods together. In some embodiments, the connectors are tubular and overlie the ends of two adjacent insulated metallic rods, while in other embodiments the connectors can have at least one end that is solid and welded to an axial end of one of the metallic rods. The metallic rods and the connectors can be stiffness matched, which can entail the connectors having an axial length that is less than a radius of curvature that results in plastic deformation of the metallic rods.

The metallic rods can comprise nitinol, for example. The connectors can also be metallic, for example comprising nitinol or titanium.

The metallic rods can be covered with a polymeric insulation layer that provides electrical insulation between adjacent metallic rods. The polymeric insulation layer can in some embodiments comprise a thermoset polymer. In some embodiments, the connectors are generally tubular and inner surfaces of the connectors are adhesively secured to outer surfaces of the polymeric insulation layer.

Some embodiments also include an outer polymeric layer, or jacket, positioned over the polymeric insulation layer. The outer polymeric can comprise a thermoplastic polymer, for example. In some embodiments, the outer polymeric layer is bonded to axial ends of the connectors. In some embodiments, the connectors include notched axial ends and the outer polymeric layer fills in and bonds to the notched axial ends of the connector to provide increased bonding surface area, enhancing both separation strength and torquability, and accomplishing matched outer diameters between rods and connectors.

In some embodiments, the metallic rods include grooves adjacent to axial ends of the metallic rods and the connectors project radially inwardly into the grooves to mechanically secure the connectors to the metallic rods. For example, the connectors can be crimped into the grooves in the metallic rods to secure them together.

In some embodiments, at least one of the connectors includes a first axial end that is welded to one of the metallic rods, and a second axial end that is adhesively secured to another one of the metallic rods. The first axial end of the connector can have a flat, solid axial face that is welded to an axial end of a metallic rod. The second axial end of the connector can include a recess and an insulated axial end of a metallic rod can be adhesively secured within the recess, such that the insulated axial end of the metallic rod is electrically insulated from the connector.

Any of the described embodiments can be used in an MRI application or in other applications wherein the guidewire is exposed to electromagnetic fields that would cause resonance and/or heating in a conventional metallic guidewire.

The foregoing and other objects, features, and advantages of the disclosed technology will become more apparent from the following detailed description, which proceeds with reference to the accompanying figures.

DETAILED DESCRIPTION

Disclosed herein are embodiments of segmented metallic guidewires that are suitable for MRI catheterization. Disclosed guidewires comprise a plurality of short conductive segments that individually are short enough and insulated from one another such that they do not resonate and/or experience undue heating during MRI. For example, the length of the conductive segments can be less than one half or one-quarter of a wavelength of RF waves used during a given MRI procedure (e.g., a 1.5T MRI scanner, a 3.0T MRI scanner, etc.), such that resonance is avoided. The resonant length can depend in part on the local varying electrical field due to the heterogeneous dielectric properties of the patient and his or her surroundings, and can depend on the length of conductive material inserted and not inserted in the body in relation to the electric field associated with in vivo MRI. The conductive segments include metallic rods that are electrically insulated from each other and mechanically coupled together end-to-end in axial alignment with mechanical connectors at each axial joint. The metallic rods and the connectors can be stiffness matched to provide a uniform degree of flexibility and strength along the guidewire.

Figure 1:
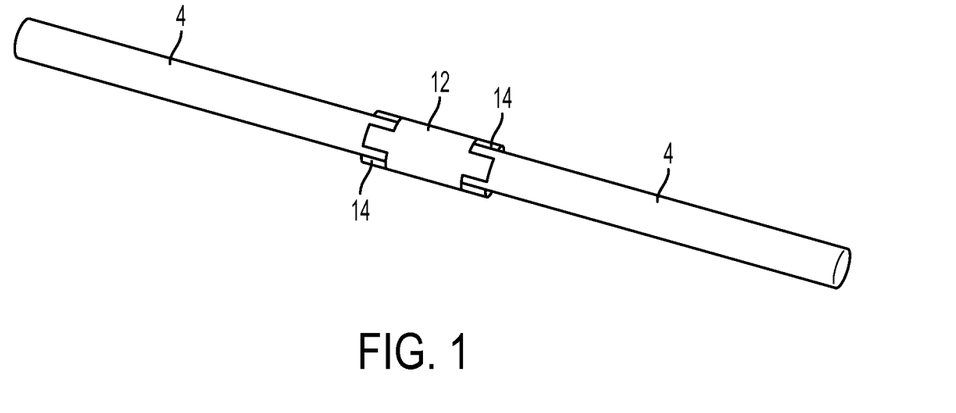
FIG. 1 shows a portion of an exemplary segmented guidewire, including two insulated metallic rods coupled together end-to-end with a tubular connector.
Figure 2:
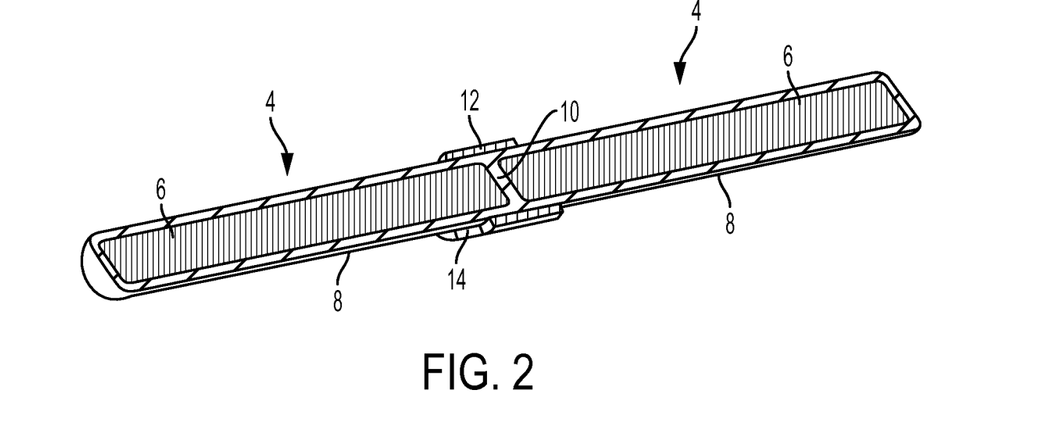
FIG. 2 is a cross-sectional view of FIG. 1 taken along a plane of the longitudinal axis of the guidewire, showing the metallic rods within each insulated segment.
Figure 3:
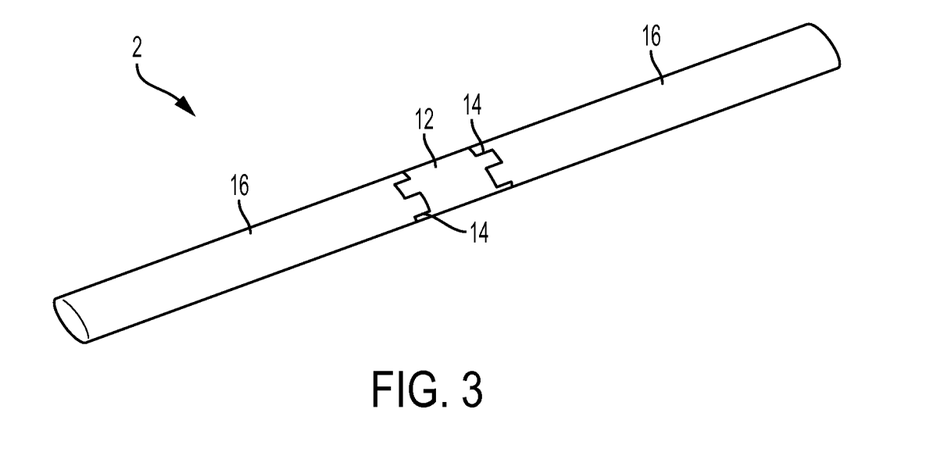
FIG. 3 shows the two segments and connector of FIG. 1, with an additional outer insulation layer provided around each segment and coupled to the connector through laser-cut patters on both ends.

FIGS. 1-3 illustrate a portion of an exemplary segmented guidewire 2 that can be used during magnetic resonance imaging (MRI) procedures. The guidewire 2 includes a plurality of electrically insulated guidewire segments 4 connected together end-to-end with connectors 12 (FIG. 1). Each segment 4 comprises an electrically conductive inner rod 6 coated with an insulation layer 8, including insulation portions 10 located between the ends of the rods 6 within the connectors 12 (FIG. 2). The insulation layer is such that it impedes electrical conduction between rods of the respective segments. The rods 6 can comprise a metallic material, such as nitinol, for example. However, the axial length of the rods 6 is short enough (e.g., less than 10 cm for 1.5T MRI scanner applications and/or less than 5 cm for 3.0T MRI scanner applications) such that they are non-resonant during an MRI procedure. The insulation layer 8 can comprise a thermoset polymer, for example, such as a polyimide or parylene thermoset polymer. In some embodiments, the insulation layer 8 can comprise a thin film polymeric coating, such as polytetrafluoroethylene (PTFE). The connectors 12 can comprise a metallic material, such as nitinol, or other MRI compatible materials (such as titanium, MP35N alloy, tungsten, tantalum, 35NLT, Elgiloy, paramagnetic stainless steel, tungsten alloys, etc.) having desired strength and flexibility properties. The inner insulation layer 8 can hold the plural rods 6 in axial alignment while providing electrical insulation between the rods. The connectors 12 are positioned around the insulation portions 10 between the rods 6 and can be secured to the insulation layer 8 with an adhesive, such as a UV cured adhesive, that bonds the inner surface of the connector to the outer surface of the insulation layer 8, as shown in FIG. 2.

The electrically insulated guidewire segments 4 can be covered by another outer insulation layer 16 (FIG. 3), which can comprise a thermoplastic polymer, such as a polyether block amide (e.g., PEBAX), high density polyethylene (HDPE), high molecular weight polyethylene (HMWPE), high molecular weight polyurethane (HMWPU), polypropylene, and/or other materials. The outer insulation layer 16 can overlie the inner insulation layer 8 and interdigitate with axially extending notches 14 on either end of the connectors 12 to provide increased surface area for bonding, increased torque strength, increased mechanical flexibility and resilience, and a uniform outer radial surface for the guidewire 2. The connectors 12 can include a ring of notches 14 around each axial end of the connector, and each notch can be filled with and bonded to the outer insulation material 16. The double insulation layer provided by the inner layer 8 and the outer layer 16 provides a redundant electrical insulation and a redundant mechanical connection between the rods 6, which enhances clinical safety of the device in the event of a connector fracture.

Figure 9:
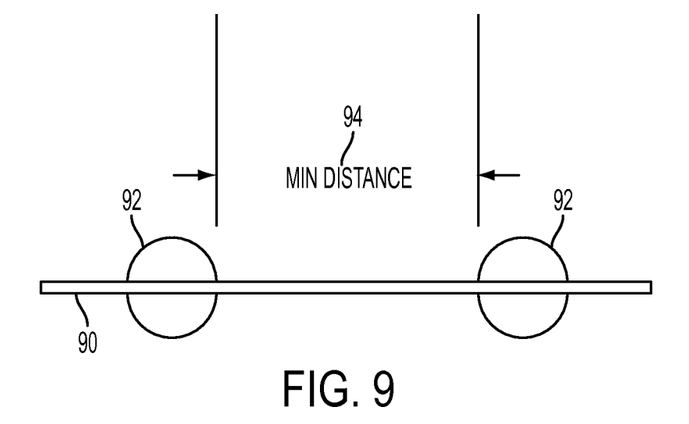
FIGS. 9 and 10 illustrate an exemplary bending testing procedure that demonstrates the stiffness-matching concept.
Figure 10:
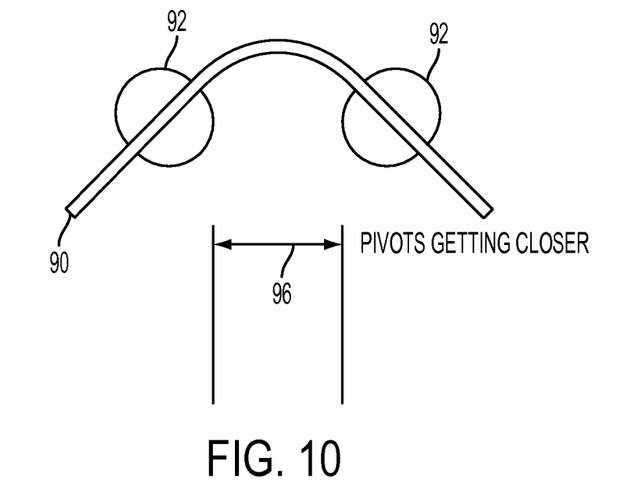

In some embodiments, the connectors 12 can be stiffness matched with the rods 6. As used herein, the term "stiffness matched" means that the axial length of a connector 12 is shorter than the radius of curvature that achieves plastic deformation of the rods 6. As illustrated in FIGS. 9 and 10, to determine the radius of curvature that achieves plastic deformation of the rods 6, a beam 90 having a diameter and material equal to the diameter and material of the rods 6 can be fixed between two rotatable grips 92 that are a distance 94 apart. The grips 92 can then be slowly moved toward each other while being allowed to freely rotate, which causes the intermediate portion of the beam 90 to bend, as shown in FIG. 10. When plastic deformation begins in the intermediate portion of the beam 90, the radius of curvature of the beam can be measured or calculated. In the example of FIG. 10, wherein the beam 90 is made of nitinol and has a diameter of 0.014", plastic deformation of the beam begins when the distance 96 between the grips 92 has been reduced to about 7 mm, which occurs when the grips have rotated about 45°. The radius of curvature can then be measured or calculated based on the distance 96 and the rotation angles of the grips. The resulting guidewires disclosed herein can exhibit smooth transitionless flexibility and enhanced column strength compared with conventional segmented guidewires not incorporating stiffness-matched connectors. The transitionless flexibility and enhanced column strength allow superior guidewire navigation of in vivo structures such as tortuous blood vessels both healthy and diseased, and also allow superior delivery of guidewire-based catheter devices.

An exemplary method of testing column strength includes fixing a distal tip of a guidewire in a rigid clamp and then pushing the guidewire from its proximal end against the rigid clamp until the wire buckles or otherwise fails. Segmented guidewires having stiffness matched metallic segments and connectors can perform better in such a column strength test (i.e., they can have higher column strength and be less likely to buckle or kink) compared to segmented guidewires not having stiffness matched metallic segments and connectors.

As used herein, the terms "distal" and "distally" refer to a location or direction that is, or a portion of a device that when implanted (for example placed within a blood vessel) is, farther away from the point of insertion into the body. The terms "proximal" and "proximally" refer to a location or direction that is, or a portion of a device that when implanted or placed within the blood vessel is, closest to the point of insertion. The terms "longitudinal" and "axial" refer to the axis extending in the distal and proximal directions, or to the longitudinal axis of a cylindrical or tubular body or lumen.

In an exemplary method for stiffness matching the rods 6 with the connectors 12, a nitinol test rod having the diameter of the rods 6 can be affixed in a stationary, non-rotational grip 30 mm away from its distal end, allowing the distal 30 mm of the test rod to extend from the grip as a cantilever. A perpendicular bending force can then be applied to the distal end of the test rod. The amount of force required to deflect the distal tip of the test rod about the fixed pivot point at the grip can be measured for certain deflection angles, such as 30°, 45°, and 60°. A similar test can also be applied to various nitinol tubes with different wall thicknesses and/or inner diameters to test matching of nitinol rods and nitinol connectors. A nitinol tube having similar flexibility to the nitinol test rod (i.e., a similar amount of force is needed to cause the same angle of deflection) can be selected as the substrate to manufacture the connectors 12. The connectors 12 can be manufactured with a total axial length less than the threshold distance 96 (e.g., 7 mm) where plastic deformation occurred in the stiffness test of FIG. 10. For example, the total axial length of the connectors 12 can be about 5 mm.

When the metallic rods and the connectors are stiffness matched, the resulting guidewire can provide a consistent level of bending and flexion as the guidewire snakes through blood vessels or other body lumens. This can avoid the problem of having a greater or lesser degree of bending at the connectors compared to the degree of bending along the segments, which can result in non-smooth curvatures and/or bending stress concentrations at the locations of greater bending.

Figure 4:
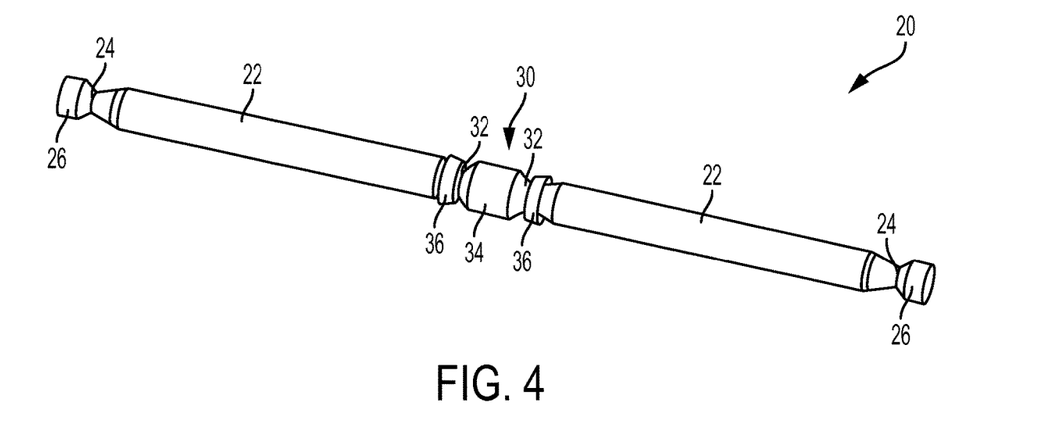
FIG. 4 shows a portion of another exemplary segmented guidewire, including two insulated metallic rods coupled together end-to-end with a crimped connector.
Figure 5:
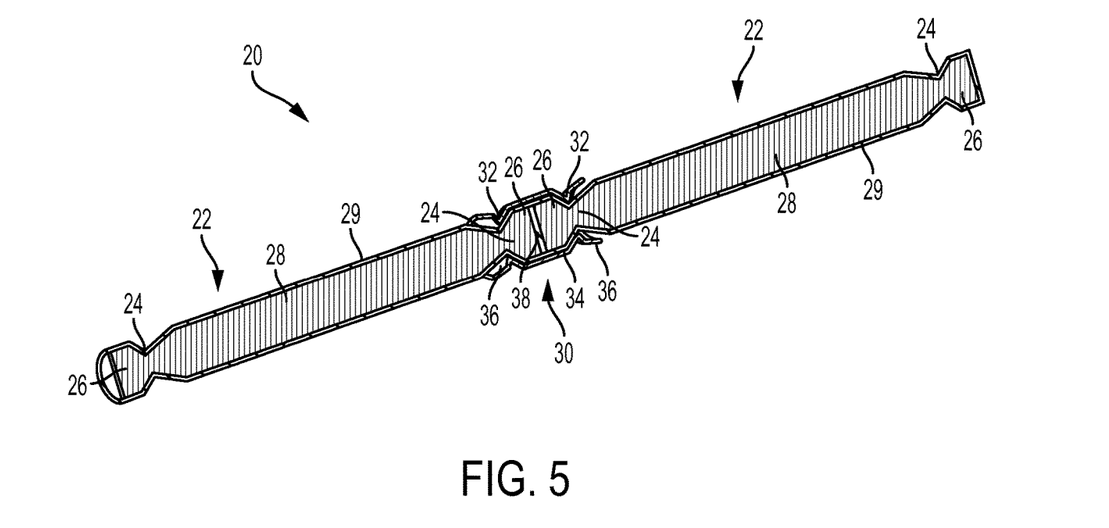
FIG. 5 is a cross-sectional view of FIG. 4 taken along a plane of a longitudinal axis of the guidewire.

FIGS. 4 and 5 illustrate another exemplary segmented guidewire 20 that is suitable for use during MRI. The guidewire 20 includes a plurality of electrically insulated guidewire segments 22 connected together end-to-end with connectors 30. Each segment 22 comprises an electrically conductive inner rod 28 covered with an insulation layer 29, including insulation portions 38 located between the ends 26 of the rods within the connectors 30 (FIG. 5). The rods 28 can comprise a metallic material, such as nitinol, for example. However, the axial length of the rods 28 is short enough (e.g., less than 10 cm and/or less than 5 cm) such that they are non-resonant during MRI. The insulation layer 29 can comprise a thermoset polymer, for example, such as a polyimide or parylene thermoset polymer. In some embodiments, the insulation layer 29 can comprise polytetrafluoroethylene (PTFE). The connectors 30 can comprise a metallic material, such as titanium, or other materials having desired strength and flexibility properties.

Each of the segments 22 can include an annular groove or other recess 24 near both axial ends 26 of the segment. Each of the connectors 30 can comprise two inwardly projecting annular ridges 32 that mate with the grooves 24 of two adjoining segments 22 to secure the segments together. An intermediate portion of the tubular connectors 30 extends between the two adjacent ridges 32 and corresponding grooves 24 and overlies insulated joint 38 between the ends 26 of the rods 28. In some embodiments, the connectors 30 also include axial end portions 36 that extend beyond the grooves 32. The connectors 30 can be positioned over adjoining ends of two segments 22 and radially crimped to create the two inwardly projecting ridges 32 that extend into the two adjacent grooves 24.

In some embodiments, the connectors can by fully tubular, such as having at least one "O" shaped cross-section that extends a full 360° around the adjoining segments. In alternative embodiments, the connectors can by not fully tubular, or incompletely circumferential, such as have a "C" shaped cross-section, that does not extend a full 360° around the adjoining segments at any point. For example, the connectors can include an axially extending slot that extends the entire length of the connector. This can allow the connector to flex in the radial dimension, allowing for some degree of radial expansion (elastic and/or plastic) and/or allowing for some degree of radially collapsing (elastic and/or plastic).

In some embodiments, the connector can be coupled to the metallic segments via tongue-and-groove slots, such tongue and groove slots extending along the longitudinal axis and/or tongue and groove slots extending along the radial axis of the guidewire. Tongue and groove connections can provide increased torque transmission and can help the guidewire resist kinking.

The grooves or other recesses 24 in the segments 22 can have various geometries. For example, in the illustrated embodiment, the grooves have an hourglass shape with a circular cross-sectional profile that varies in diameter. In other embodiments, the segments 22 can include recesses that form non-circular cross-sections, such a polygonal or elliptical cross-section. Recesses forming non-circular cross-sections can provide resistances to rotational slipping between the segments and the connectors, and thereby increase torsional strength across the joints.

In some embodiments, the guidewire 20 can also include an additional outer insulation layer (not shown) that overlies the layer 29 and fill the region between the connectors, thereby providing a more constant outer diameter along the guidewire, increased torque strength, increased mechanical flexibility and resilience, and/or redundancy in case of mechanical failure.

The segments 22 and connectors 30 can be stiffness matched in the same way as is described above, even though the connectors 30 can be made of a different metal (e.g., titanium) than the rods 28 (e.g., nitinol) or can be made of stiff, non-conductive materials such as PEEK or ceramic materials. The axial length of the connectors 30 can be less than the radius of curvature that results in plastic deformation of the rods 28 (e.g., less than 7 mm), and the wall thickness of the connectors can be selected to provide a similar flexibility to the rods.

Figure 6:
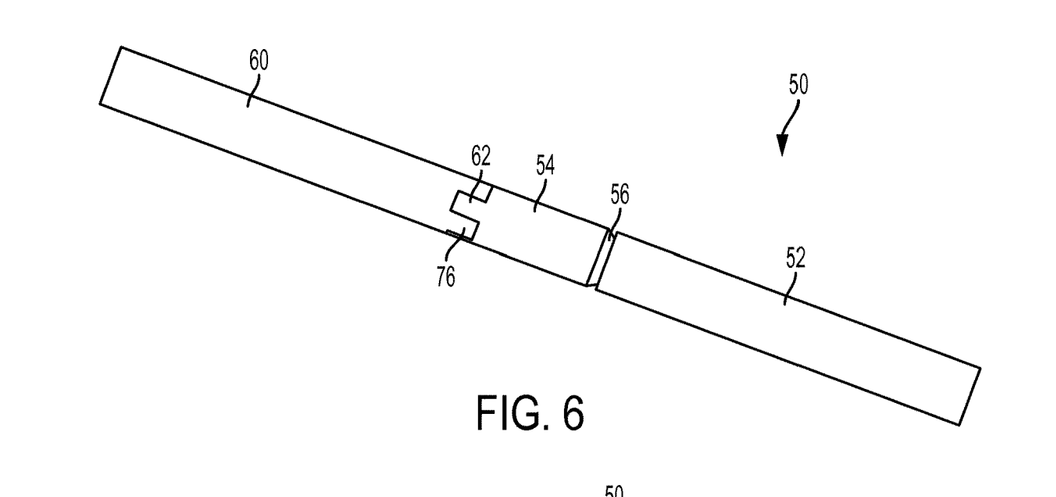
FIG. 6 show a portion of another exemplary segmented guidewire, including one metallic segment welded to a connector and a second insulated metallic segment adhesively secured to the connector.
Figure 7:
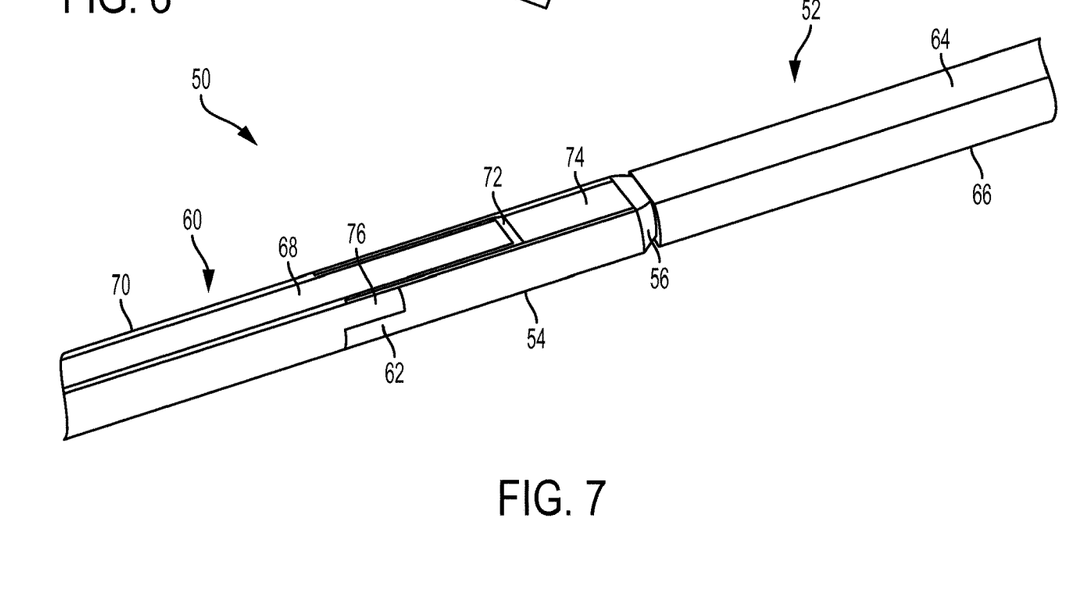
FIG. 7 is a cross-sectional view of FIG. 6 taken along a plane parallel to a longitudinal axis of the guidewire.

FIGS. 6 and 7 illustrate another exemplary segmented guidewire 50 that is suitable for use during MRI. The guidewire 50 includes a plurality of electrically insulated guidewire segments 52, 60 connected together end-to-end with tubular connectors 54 that overlap the adjoining ends of the segments. FIG. 7 shows the two segments 52, 60 and the connector 54 in a cross-sectional view taken along a plane parallel with the longitudinal axis of the guidewire. Each segment 52, 60 comprises an electrically conductive inner rod 64, 68, respectively, covered with an insulation layer 66, 70, respectively. The rods 64, 68 can comprise a conductive metallic material, such as nitinol, for example. However, the rods are electrically short enough (e.g., less than 10 cm and/or less than ¼ wavelength) such that they are non-resonant during MRI. The insulation layers 66 and 70 can comprise a thermoset polymer, for example. The connectors 30 can comprise a metallic material, such as nitinol, or other materials having desired strength and flexibility properties.

The segments 52 and 60 can be secured to the connector 54 in different ways. The segment 52 can include an uncovered, or bare, end portion 74 of the metallic rod 64 that extends into one end of the tubular connector 54. The axial end of the connector 54 can be laser welded to the bare surface of the end portion 74 of the rod, forming an annular weld 56 that extends around the surface of the rod. Thus, the interface between the rod end portion 74 and the overlapping connector 54 may be electrically conductive such that the rod 64 is not insulated from the connector 54.

The insulated segment 60, fully covered with an electrically insulating layer 70, can be inserted into the other end of the tubular connector 54 and secured to the connector using an adhesive, such as a UV cured adhesive. As shown in FIG. 7, the insulated axial end 72 of the segment is positioned against the uncovered bare end portion 74 of the rod 64. The connector 54 can include notches 62 at end overlying the segment 60, and the notches 62 can be interdigitated with an additional layer of thermoplastic polymer insulation to enhance the torque response, provide an even outer radial surface, increase flexibility and strength, and provide redundancy in case of mechanical failure.

The segments 52, 60 and connectors 54 can be stiffness matched in the same way as is described above with reference to FIGS. 9 and 10. The axial length of the tubular connectors 54 can be less than the radius of curvature that results in plastic deformation of the rods 64, 68 (e.g., less than 7 mm), and the wall thickness of the connectors can be selected to provide a similar flexibility to the rods.

Figure 8:
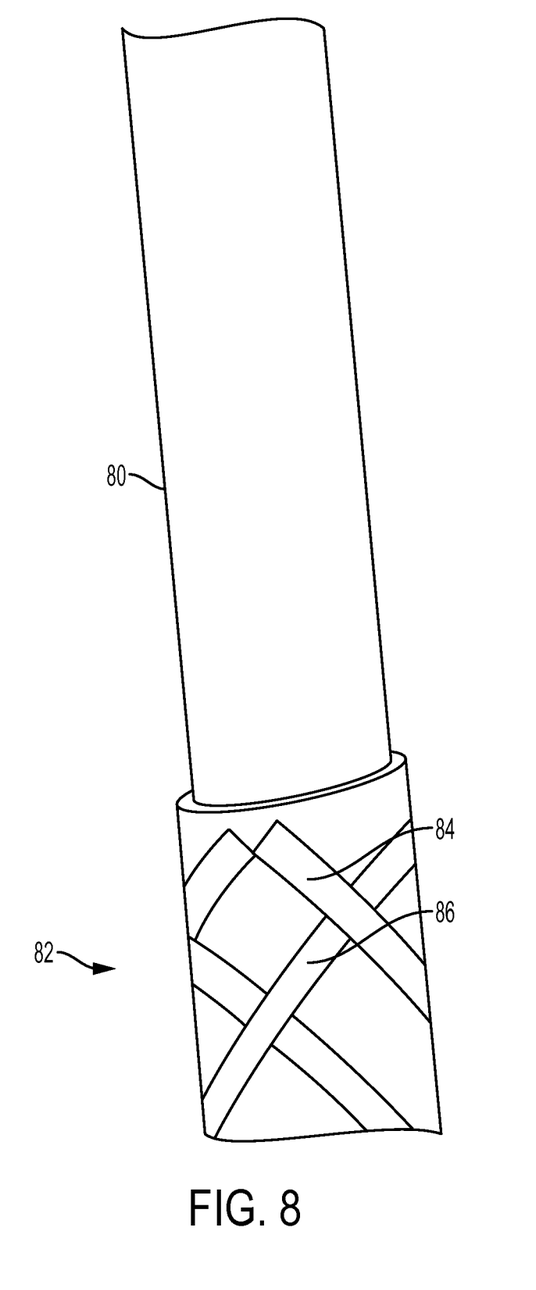
FIG. 8 shows an exemplary metallic rod with a braided outer insulation layer.

In any of the embodiments disclosed herein, the connected metallic rod assemblies that make up the guidewire can be covered and supported by a non-metallic braiding layer, an example of which is shown in FIG. 8. In FIG. 8, an exemplary metallic rod segment and connector assembly 80 is covered with a non-metallic braiding 82 that includes helical stands 86 and 84 that extend in opposing helical directions around the rod 80 to form a braided outer layer. Such an outer layer 82 can provide enhanced safety in case the connector breaks or fractures so that the guidewire stays intact, stays insulated, and can be retracted as a unit out of a patient. The outer layer 82 can also provide enhanced flexibility, supplemental electrical insulation, and torque control for the guidewire, as well as providing a substantially smooth outer radial surface. In certain embodiments, the diameter of the guidewire segments is substantially constant along a substantial portion of the axial length of the guidewire, such that a substantial portion of the length of the guidewire does not taper toward the distal end of that portion of the guidewire, even though another portion of the guidewire may be tapered. In certain embodiments, the distal segment can be tapered to accomplish desired mechanical properties, such as atraumatic tip, shapable tip, flexibility, or curved geometry. The outer layer 82 can comprise various non-conductive materials, such as vectran, nylon, delrin, kevlar, or teflon, or can comprise braided non-conductive combinations of such materials.

In any of the embodiments disclosed herein, the guidewire can include markers that provide visibility within the body during MRI. The guidewire can include any number of MRI susceptibility markers located periodically along the length of the guidewire, such as at the rods and/or at the connectors. Such markers can comprise iron-oxide or other paramagnetic compounds that provide MRI conspicuity using susceptibility-weighted imaging (i.e., "black markers"), and/or can comprise inductive ("wireless") resonators to serve as "white" markers.

Figure 11:
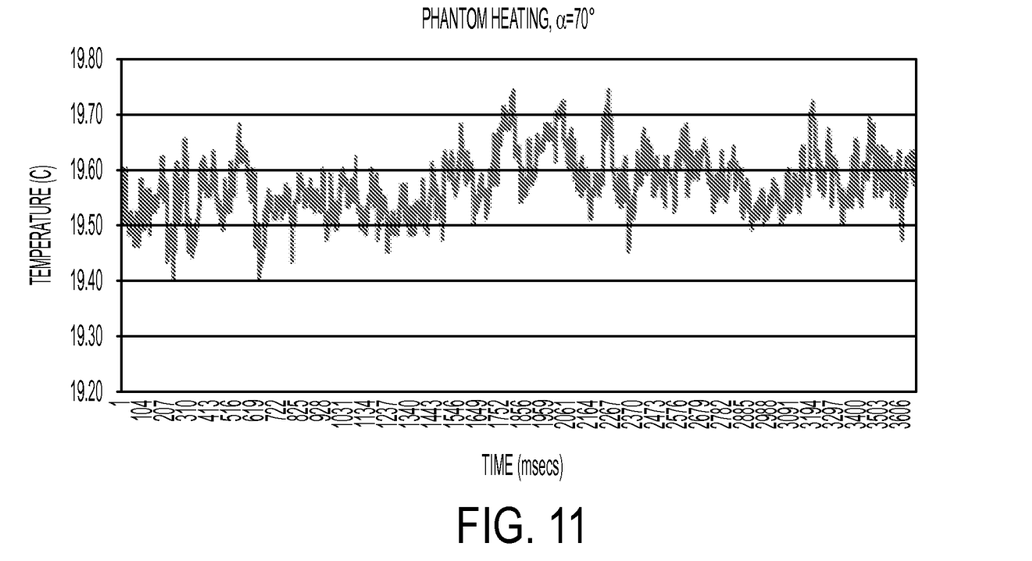
FIGS. 11 and 12 illustrate the resistance of disclosed guidewire embodiments to heating during MRI exposure.
Figure 12:
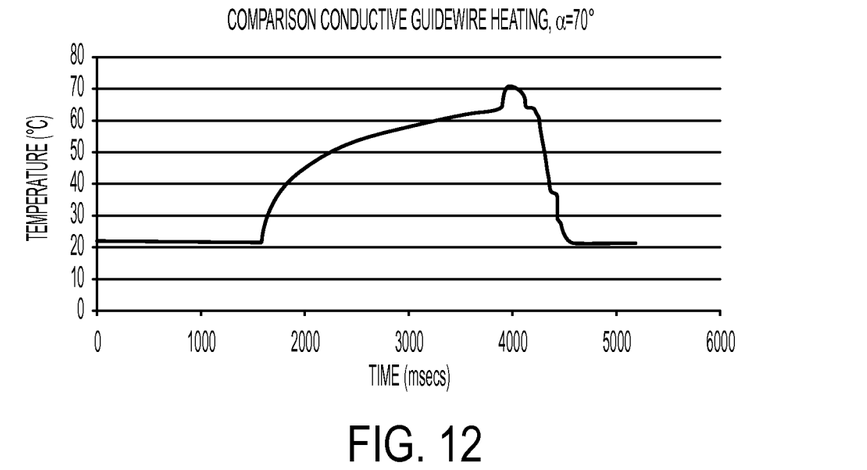

FIG. 11 is a graph showing change in temperature over time in a disclosed segmented metallic guidewire during MRI. This data was collected using an ASTM F2182 Phantom acrylic MRI testing device, with a 5" horizontal offset from isocenter, where the local E fields are maximum, and with a MRI SSFP flip angle of 70°. As shown in the graph, the temperature stayed between 19° C. and 20° C. over more than 3600 msecs of MRI exposure. This data can be compared to the data shown in FIG. 12 for a conventional conductive metallic guidewire, a NHLBI TST-035 guidewire having the detuning/decoupling circuitry removed. As shown in FIG. 12, the temperature of the conventional metallic guidewire increased dramatically from about 22° C. up to more than 70° C. in less than 3000 msecs of MRI exposure.

The disclosed segmented guidewires can also avoid excessive heating caused by other types of radiofrequency excitation and other electromagnetic fields due to the insulation between the short metallic segments.

The disclosed stiffness-matched guidewires can be used to facilitate MRI catheterization procedures, where catheters are directed through the body under guidance by MRI instead of conventional alternatives such as X-ray. MRI catheterization allows catheter devices to be navigated through the body while imaging both visualized devices and soft tissue, unlike X-ray navigation. MRI catheterization also allows radiation-free procedures, which is desirable for use in children to reduce the risk of cancer caused by ionizing radiation, and to reduce radiation exposure to patients and staff during complex and protracted procedures. Stiffness-matched MRI guidewires can be used as wire guides to help catheters navigate vascular and non-vascular structures. They can be visualized "passively" based on intrinsic materials properties under MRI, without complex electronics used in "active" MRI catheter devices. MRI catheterization using the disclosed technology can be employed in patients to combine catheter navigation through cardiovascular structures using real-time MRI to measure pressure, along with high-fidelity cardiac flow and function measurements afforded by MRI. The disclosed invention can be used safely to guide both diagnostic and therapeutic devices (catheters, stents, cardiac occluder devices, bioptomes, ablation devices) to their intended targets using MRI, as well as using conventional X-ray guidance in case of combined or bailout X-ray procedures. Beyond MRI catheterization applications, resonant-free devices can be employed for example during microwave energy application to ablate pathological tissue, and MRI-safe devices may be employed when magnetic attraction is employed in catheter and minimally invasive procedures for example to dock nearby devices across soft tissue structures as in the SentreHeart Lariat endo- and epi-wire docking system.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Integers, characteristics, materials, and other features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

The singular terms "a", "an", and "the" include plural referents unless context clearly indicates otherwise. The term "comprises" means "includes without limitation." The term "coupled" means physically linked and does not exclude intermediate elements between the coupled elements. The term "and/or" means any one or more of the elements listed. Thus, the term "A and/or B" means "A", "B" or "A and B."

Although methods and materials similar or equivalent to those described herein can be used in the practice or testing of the present technology, only certain suitable methods and materials are described herein. In case of conflict, the present specification, including terms, will control. In addition, the materials, methods, and devices are illustrative only and not intended to be limiting.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims. We therefore claim all that comes within the scope of these claims.

The invention claimed is:

1. A segmented guidewire for use in medical applications, comprising:
   a plurality of elongated metallic rods positioned in axial, end-to-end alignment along a longitudinal axis of the guidewire;
   a polymeric insulation layer that surrounds the metallic rods and separates adjacent axial ends of the metallic rods such that the metallic rods are electrically insulated from one another;
   a plurality of tubular metallic connectors, each connector being positioned around the insulation layer at a joint between two adjacent axial ends of two of the insulated metallic rods such that the connector overlaps the insulation layer and the two adjacent axial ends of the two metallic rods and secures the two metallic rods together without electrically coupling the two metallic rods together; and
   an outer layer comprising polymeric material that is positioned around the polymeric insulation layer and between axial ends of the connectors, such that the segmented guidewire has a uniform outer diameter that is defined by the connectors and the outer layer.

2. The guidewire of claim 1, wherein the metallic rods and the connectors are stiffness matched.

3. The guidewire of claim 2, wherein the connectors have an axial length that is less than a radius of curvature that results in plastic deformation of the metallic rods.

4. The guidewire of claim 1, wherein the polymeric insulation layer comprises a thermoset polymer.

5. The guidewire of claim 1, wherein inner surfaces of the connectors are adhesively secured to outer surfaces of the polymeric insulation layer.

6. The guidewire of claim 1, wherein the connectors each comprise two opposing axial ends, wherein each axial end of the connectors comprises an annular rim that includes a plurality of notches, and wherein the outer layer extends into the plurality of notches.

7. The guidewire of claim 1, wherein the metallic rods include grooves adjacent to the axial ends of the metallic rods and the connectors project radially inwardly into the grooves to mechanically secure the connectors to the metallic rods.

8. The guidewire of claim 7, wherein the connectors are crimped into the grooves in the metallic rods.

9. The guidewire of claim 1, wherein the outer layer comprises a braided polymeric outer layer.

10. A method comprising performing magnetic resonance imaging on a portion of a subject while the guidewire of claim 1 is partially or completely inside the portion of the subject.

11. The guidewire of claim 1, wherein the connectors comprise electrically non-conductive material.

12. The guidewire of claim 1, wherein the outer layer does not overlap the connectors.

13. The guidewire of claim 1, wherein the outer layer and the connectors have an equal inner diameter.

14. The guidewire of claim 1, wherein the insulation layer has a uniform outer diameter.

15. A segmented guidewire for use in medical applications, comprising:
   a plurality of elongated metallic rods positioned in axial, end-to-end alignment along a longitudinal axis of the guidewire, wherein each of the metallic rods are electrically insulated from one other; and
   a plurality of metallic connectors, each connector positioned at a joint between two adjacent axial ends of two of the insulated metallic rods such that each connector secures the two metallic rods together; and
   wherein the metallic rods and the connectors are stiffness matched, such that an axial length of the connectors is shorter than a radius of curvature that achieves plastic deformation of the rods.

16. The guidewire of claim 15, wherein the connectors are tubular.

17. The guidewire of claim 15, wherein the metallic rods and the connectors are made of the same metallic material.

18. The guidewire of claim 17, wherein the metallic rods and the connectors are made of nitinol.

19. The guidewire of claim 15, wherein the metallic rods and the connectors are made of different metallic materials.

20. The guidewire of claim 19, wherein the metallic rods are made of nitinol and the connectors are made of titanium or paramagnetic stainless steel.

21. The guidewire of claim 15, wherein at least some of the metallic rods are covered with a polymeric insulation layer that provides electrical insulation between adjacent metallic rods.

22. The guidewire of claim 21, wherein the polymeric insulation layer comprises an inner polymeric insulation layer, the guidewire further comprising an outer polymeric layer positioned over the inner polymeric insulation layer.

23. The guidewire of claim 22, wherein the connectors include at least one axial end that comprises an annular rim that includes a plurality of notches extending circumferentially around a metallic rod, and the outer polymeric layer fills in the notches.

24. The guidewire of claim 15, wherein the metallic rods and the connectors are covered by a non-metallic braided polymeric outer layer.

25. The guidewire of claim 15, wherein the axial length of the connectors is less than 7 mm.

26. A segmented guidewire for use in medical applications, comprising:
a plurality of elongated metallic rods positioned in axial, end-to-end alignment along a longitudinal axis of the guidewire; and
a plurality of metallic connectors, each connector positioned at a joint between two adjacent axial ends of two of the metallic rods, wherein each of the connectors has a first axial end that is adhesively bonded to an electrically insulated end portion of one of the metallic rods such that the metallic rod is electrically insulated from the first axial end of the connector, and wherein each connector has a second axial end that is welded to an uninsulated end portion of another of the metallic rods, such that the connector secures the two metallic rods together by both adhesion and welding without electrically coupling the two metallic rods together;
wherein the first axial end of each connector comprises an annular rim that includes a plurality of notches that extend circumferentially around the insulated end portion of the metallic rod, and the metallic rod is covered with a polymeric jacket that fills in the plurality of notches in the annular rim of the connector.

27. The guidewire of claim 26, wherein the metallic rods and the connectors are stiffness matched and the connectors have an axial length that is less than a radius of curvature that results in plastic deformation of the metallic rods.

28. The guidewire of claim 26, wherein the first axial end of the connector is tubular and overlaps the insulated end portion of one of the metallic rods.

29. The guidewire of claim 26, wherein the second axial end of the connector is tubular and overlaps the uninsulated end portion of the metallic rod that is welded to the connector.

30. The guidewire of claim 26, wherein the segmented guidewire has a uniform outer diameter that is defined by the connectors and the polymeric jacket, which have equal outer diameters.

* * * * *